(12) United States Patent
Ho et al.

(10) Patent No.: US 11,969,450 B2
(45) Date of Patent: Apr. 30, 2024

(54) METHODS FOR IMPROVING GASTROINTESTINAL BARRIER FUNCTION AND INHIBITING GROWTH OF ENTERIC PATHOGENIC BACTERIA

(71) Applicant: GLAC BIOTECH CO., LTD., Tainan (TW)

(72) Inventors: Hsieh-Hsun Ho, Tainan (TW); Jui-Fen Chen, Tainan (TW); Yi-Wei Kuo, Tainan (TW); Chi-Huei Lin, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 0 days.

(21) Appl. No.: 17/730,665

(22) Filed: Apr. 27, 2022

(65) Prior Publication Data

US 2023/0201280 A1 Jun. 29, 2023

(30) Foreign Application Priority Data

Dec. 23, 2021 (TW) ................................. 110148434

(51) Int. Cl.
*A61K 35/747* (2015.01)
*A23L 33/135* (2016.01)
*A61K 35/745* (2015.01)

(52) U.S. Cl.
CPC .......... *A61K 35/747* (2013.01); *A23L 33/135* (2016.08); *A61K 35/745* (2013.01); *A23V 2002/00* (2013.01); *A23V 2400/175* (2023.08); *A23V 2400/515* (2023.08);

(Continued)

(58) Field of Classification Search
CPC ... A61K 35/747; A61K 35/745; A23L 33/135; A23V 2002/00; A23Y 2220/73; A23Y 2300/21; A23Y 2300/45; A23Y 2300/49; A23Y 2300/55

See application file for complete search history.

(56) References Cited

FOREIGN PATENT DOCUMENTS

CN 102604854 A * 7/2012 ........... A23L 33/135
EP 904784 A1 * 3/1999 ........... A23L 1/0345

OTHER PUBLICATIONS

Ho, Hsieh. (2020). The Postbiotics, Totipro PE0401, and Probiotic Mixture, PF1001, Modulate the Gut Microbiota and Ameliorate Diarrhea in Weaning Piglets. Biomedical Journal of Scientific & Technical Research. 28. 10.26717/BJSTR.2020.28.004584. (Year: 2020).*

(Continued)

*Primary Examiner* — Thomas J. Visone
(74) *Attorney, Agent, or Firm* — HSML P.C.

(57) ABSTRACT

Disclosed herein are methods for improving gastrointestinal barrier function, alleviating a gastrointestinal barrier dysfunction-associated disorder, and inhibiting growth of enteric pathogenic bacteria using a composition containing *Lactobacillus rhamnosus* MP108, *Bifidobacterium longum* subsp. *infantis* BLI-02, and *Bifidobacterium animalis* subsp. *lactis* BB-115, which are deposited at the China General Microbiological Culture Collection Center (CGMCC) respectively under accession numbers CGMCC 21225, CGMCC 15212, and CGMCC 21840. A number ratio of *Lactobacillus rhamnosus* MP108, *Bifidobacterium longum* subsp. *infantis* BLI-02, and *Bifidobacterium animalis* subsp. *lactis* BB-115 ranges from 1:0.2:0.67 to 1:9:9.

10 Claims, 3 Drawing Sheets

Specification includes a Sequence Listing.

(52) U.S. Cl.
CPC ... *A23V 2400/529* (2023.08); *A23V 2400/531* (2023.08); *A23V 2400/533* (2023.08)

(56) References Cited

OTHER PUBLICATIONS

Daniel M. Commane, et al., Effects of Fermentation Products of Pro-and Prebiotics on Trans-Epithelial Electrical Resistance in an in Vitro Model of the Colon, Nutrition Cancer. 2005; 51(1): 102-109.
Xu Han, et al., Lactobacillus rhamnosus GG prevents epithelial barrier dysfunction induced by interferon-gamma and fecal supernatants from irritable bowel syndrome patients in human intestinal enteroids and colonoids, Gut Microbes. 2019; 10(1): 59-76.
Pei-Shan Hsieh, et al., *Lactobacillus* spp. reduces ethanol-induced liver oxidative stress and inflammation in a mouse model of alcoholic steatohepatitis, Experimental and Therapeutic Medicine, Mar. 2021; 21(3):188.
Y.-T. Chen, et al., Antibacterial activity of viable and heat-killed probiotic strains against oral pathogens, Letters in Applied Microbiology. Apr. 2020; 70(4):310-317.

* cited by examiner

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Forward primer CLDN1-F for CLDN1 gene

<400> SEQUENCE: 1
gcgcgatatt tcttcttgca gg                                        22

<210> SEQ ID NO 2
<211> LENGTH: 21
<212> TYPE: DNA
<213> ORGANISM: Artificial Sequence
<220> FEATURE:
<223> OTHER INFORMATION: Reverse primer CLDN1-R for CLDN1 gene

<400> SEQUENCE: 2
ttcgtacctg gcattgactg g                                         21

<210> SEQ ID NO 3
<211> LENGTH: 18
<212> TYPE: DNA
<213> ORGANISM: Artificial Sequence
<220> FEATURE:
<223> OTHER INFORMATION: Forward primer GAPDH-F for GAPDH gene

<400> SEQUENCE: 3
gaaggtgaag gtcggagt                                             18

<210> SEQ ID NO 4
<211> LENGTH: 19
<212> TYPE: DNA
<213> ORGANISM: Artificial Sequence
<220> FEATURE:
<223> OTHER INFORMATION: Reverse primer GAPDH-R for GAPDH gene

<400> SEQUENCE: 4
gaagatggtg atggatttc                                            19

METHODS FOR IMPROVING GASTROINTESTINAL BARRIER FUNCTION AND INHIBITING GROWTH OF ENTERIC PATHOGENIC BACTERIA

CROSS-REFERENCE TO RELATED APPLICATION

This application claims priority of Taiwanese Invention Patent Application No. 110148434, filed on Dec. 23, 2021.

FIELD

The present disclosure relates methods for improving gastrointestinal barrier function, alleviating a gastrointestinal barrier dysfunction-associated disorder, and inhibiting growth of enteric pathogenic bacteria using a composition containing three lactic acid bacterial strains.

BACKGROUND

The gastrointestinal barrier, which is composed of gastrointestinal epithelial cells linked by tight junction proteins (in particular claudins), can block the entry of gastrointestinal pathogens and secretions thereof. Gastrointestinal dysbiosis would cause the proliferation of gastrointestinal pathogens. Gastrointestinal pathogens might damage the structure and function of the gastrointestinal epithelium by down-regulating the expression of tight junction proteins, and might undesirably enhance the permeability of the gastrointestinal tract, resulting in bacterial infections and gastrointestinal barrier dysfunction-associated disorders (e.g., inflammatory bowel disease (IBD) (such as ulcerative colitis (UC) and Crohn's disease) and irritable bowel syndrome (IBS))

Gastrointestinal barrier dysfunction-associated disorders are typically treated with antibiotics. However, these antibiotics might cause enteric pathogens to develop antibiotic resistance, and might cause severe side effects and adverse effects.

Probiotics are resident normal flora of the intestinal tract and believed to play important roles in regulating proper intestinal immunity and digestion by balancing intestinal microflora. These beneficial microorganisms are widely used as live microbial dietary supplements and can help restoring intestinal microfloral balance. Many species of lactic acid bacteria (LAB) are conferred with the generally recognized as safe (GRAS) status, and are widely used as probiotics. Common LAB include *Lactobacillus* spp., *Lactococcus* spp., *Pediococcus* spp., *Streptococcus* spp., *Enterococcus* spp., *Bifidobacterium* spp., *Bacillus* spp., *Leuconostoc* spp., etc.

Previous studies have demonstrated that certain strains of LAB are effective in preventing or alleviating gastrointestinal barrier dysfunction-associated disorders. For example, it has been reported in D. M. Commane et al. (2005), *Nutrition and Cancer*, 51(1):102-109 that *Bifidobacterium animalis* subsp. *lactis* BB-12 has been demonstrated to have ability to increase the transepithelial electrical resistance (TEER) level of the human colon adenocarcinoma cell line Caco-2 having deoxycholic acid (DCA)-induced intestinal epithelial barrier damage, hence being capable of effectively improving the integrity and function of the gastrointestinal epithelium and the tight junction proteins and preventing or alleviating gastrointestinal barrier dysfunction-associated disorders.

In addition, it has been reported in X. Han et al. (2019), *Gut Microbes.*, 10(1):59-76 that *Lactobacillus rhamnosus* GG (LGG) has been demonstrated to have ability to improve the permeability of the intestinal epithelium in human intestinal epithelial cultures (i.e., enteroids and colonoids) having interferon-γ (INF-γ)-induced epithelial barrier damage, and to normalize tight junction protein expression, hence being capable of effectively preventing or alleviating gastrointestinal barrier dysfunction-associated disorders.

In spite of the aforesaid, there is still a need to develop a new strategy that can be utilized for improving gastrointestinal barrier function, alleviating a gastrointestinal barrier dysfunction-associated disorder, and inhibiting growth of enteric pathogenic bacteria.

SUMMARY

Therefore, in a first aspect, the present disclosure provides a method for improving gastrointestinal barrier function which can alleviate at least one of the drawbacks of the prior art.

The method includes administering to a subject in need thereof a composition containing *Lactobacillus rhamrnosus* MP108, *Bifidobacterium longum* subsp. *infantis* BLI-02, and *Bifidobacterium animalis* subsp. *lactis* BB-115, which are deposited at the China General Microbiological Culture Collection Center (CGMCC) respectively under accession numbers CGMCC 21225, CGMCC 15212, and CGMCC 21840. A number ratio of *Lactobacillus rhamnosus* MP108, *Bifidobacterium longum* subsp. *infantis* BLI-02, and *Bifidobacterium animalis* subsp. *lactis* BB-115 ranges from 1:0.2:0.67 to 1:9:9.

In a second aspect, the present disclosure provides a method for alleviating a gastrointestinal barrier dysfunction-associated disorder, which can alleviate at least one of the drawbacks of the prior art, and which includes administering to a subject in need thereof the aforesaid composition.

In a third aspect, the present disclosure provides a method for inhibiting growth of enteric pathogenic bacteria, which can alleviate at least one of the drawbacks of the prior art, and which includes administering to a subject in need thereof the aforesaid composition.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
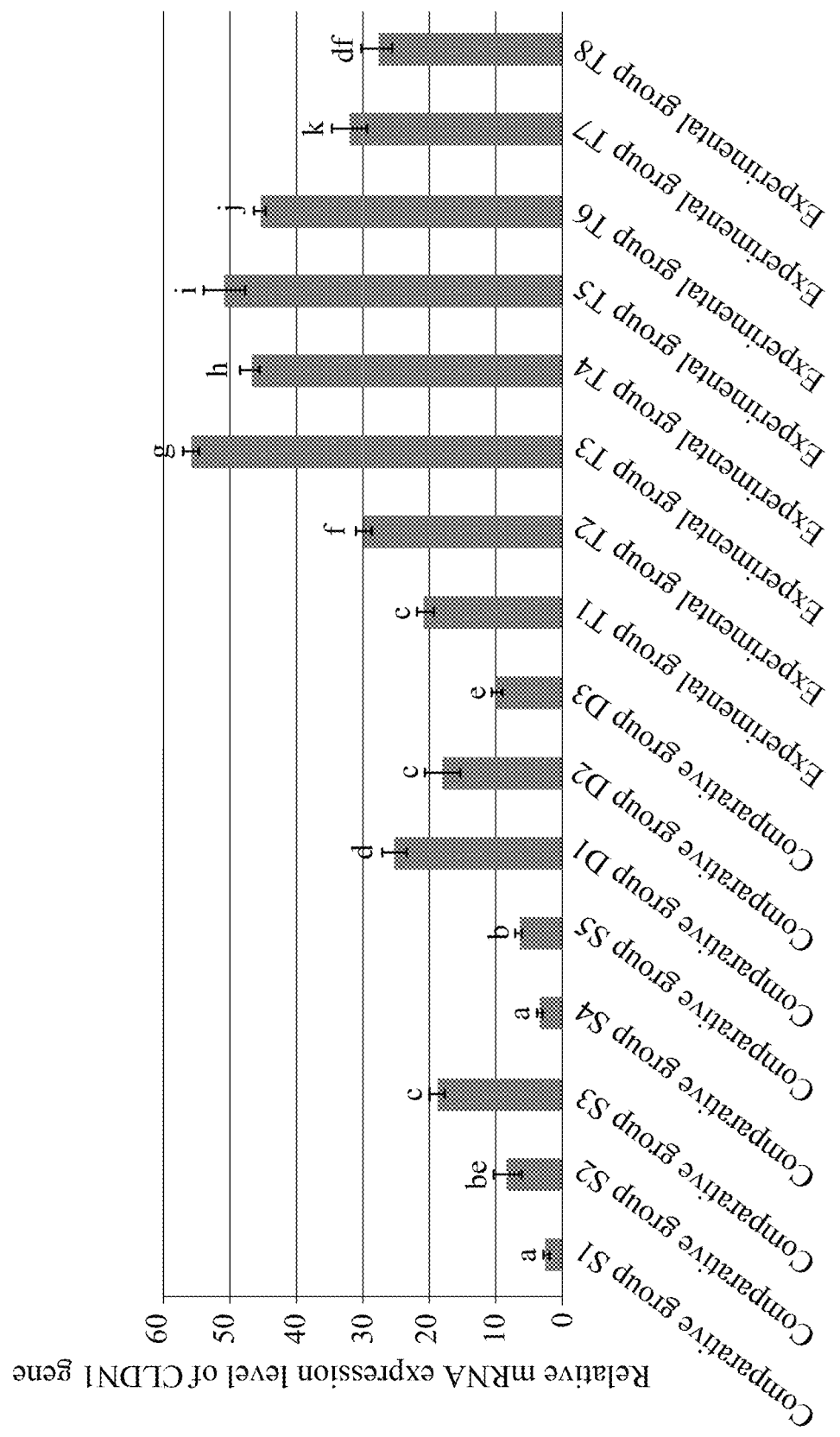
FIG. 1 shows a relative mRNA expression level of CLDN1 gene in each group of Example 1, infra, in which: the English letters indicate the results of statistical analysis; if two groups have any same English letter, there is no significant difference between the two groups; and if two groups do not have any same English letter, there is a significant difference between the two groups ($p<0.05$)

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a method for improving gastrointestinal barrier function, which includes administering to a subject in need thereof a composition containing *Lactobacillus rhamnosus* MP108, *Bifidobacterium longum* subsp. *infantis* BLI-02, and *Bifidobacterium animalis* subsp. *lactis* BB-115, which are deposited at the China General Microbiological Culture Collection Center (CGMCC) respectively under accession numbers CGMCC 21225, CGMCC 15212, and CGMCC 21840. A number ratio of *Lactobacillus rhamnosus* MP108, *Bifidobacterium longum* subsp. *infantis* BLI-02, and *Bifidobacterium animalis* subsp. *lactis* BB-115 ranges from 1:0.2:0.67 to 1:9:9.

As used herein, the term "administering" or "administration" means introducing, providing or delivering the above-mentioned composition to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

In certain embodiments, the number ratio of *Lactobacillus rhamnosus* MP108, *Bifidobacterium longum* subsp. *infantis* BLI-02, and *Bifidobacterium animalis* subsp. *lactis* BB-115 ranges from 1:0.67:0.67 to 1:1.5:1.5. In an exemplary embodiment, the number ratio of *Lactobacillus rhamnosus* MP108, *Bifidobacterium longum* subsp. *infantis* BLI-02, and *Bifidobacterium animalis* subsp. *lactis* BB-115 is 1:0.67:1. In another exemplary embodiment, the number ratio of *Lactobacillus rhamnosus* MP108, *Bifidobacterium longum* subsp. *infantis* BLI-02, and *Bifidobacterium animalis* subsp. *lactis* BB-115 is 1:1:1.

As used herein, the term "gastrointestinal barrier function" can be used interchangeably with other terms such as "gastrointestinal epithelial barrier function" and "intestinal barrier function".

According to the present disclosure, the improvement of the gastrointestinal barrier function may include at least one of the following: improving the structure and function of the gastrointestinal tract epithelium, protection against gastrointestinal pathogenic bacteria infection, promoting the colonization of probiotics, and regulating gastrointestinal microflora.

According to the present disclosure, the composition may have a total bacterial concentration ranging from $1 \times 10^7$ CFU/mL to $1 \times 10^{12}$ CFU/mL. In certain embodiments, the composition may have a total bacterial concentration ranging from $1 \times 10^8$ CFU/mL to $1 \times 10^{10}$ CFU/mL. In an exemplary embodiment, the composition may have a total bacterial concentration of $10^9$ CFU/mL.

According to the present disclosure, *Lactobacillus rhamnosus* MP108, *Bifidobacterium longum* subsp. *infantis* BLI-02, and *Bifidobacterium animalis* subsp. *lactis* BB-115 may be live cells or dead cells, concentrated or non-concentrated, a liquid, a paste, a semi-solid, or a solid (e.g., a pellet, a granule, or a powder), and may be heat-inactivated, frozen, dried, or freeze-dried (e.g., may be in freeze-dried form or spray/fluid bed dried form).

According to the present disclosure, the composition may be formulated as a food product using a standard technique well known to one of ordinary skill in the art. For example, the composition may be directly added to an edible material or may be used to prepare an intermediate composition (e.g., a food additive or a premix) suitable to be subsequently added to the edible material.

As used herein, the term "food product" refers to any article or substance that can be ingested by a subject into the body thereof. Examples of the food product may include, but are not limited to, milk powders, fermented milk, yogurt, butter, beverages (e.g., tea, coffee, etc.), functional beverages, a flour product, baked foods, confectionery, candies, fermented foods, animal feeds, health foods, infant foods, and dietary supplements.

According to the present disclosure, the composition may be prepared in the form of a pharmaceutical composition. The pharmaceutical composition may be formulated into a suitable dosage form for oral, parenteral or topical administration using technology well known to those skilled in the art.

According to the present disclosure, the suitable dosage form for oral administration includes, but is not limited to, sterile powders, tablets, troches, lozenges, pellets, capsules, dispersible powders or granules, solutions, suspensions, emulsions, syrup, elixir, slurry, and the like.

For parenteral administration, the pharmaceutical composition according to the present disclosure may be formulated into an injection, e.g., a sterile aqueous solution or a dispersion.

The pharmaceutical composition according to the present disclosure may be administered via one of the following parenteral routes: intraperitoneal injection, intrapleural injection, intramuscular injection, intravenous injection, intraarterial injection, intraarticular injection, intrasynovial injection, intrathecal injection, intracranial injection, intraepidermal injection, subcutaneous injection, intradermal injection, intralesional injection, and sublingual administration. In certain embodiments, the pharmaceutical composition may be administered via intralesional injection.

According to the present disclosure, the pharmaceutical composition may be formulated into an external preparation suitable for topical application to the skin using technology well known to those skilled in the art. The external preparation includes, but is not limited to, emulsions, gels, ointments, creams, patches, liniments, powder, aerosols, sprays, lotions, serums, pastes, foams, drops, suspensions, salves, and bandages.

The pharmaceutical composition according to the present disclosure may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, fillers, wetting agents, lubricants, absorption delaying agents, liposomes, and the like. The choice and amount of the aforesaid agents are within the expertise and routine skills of those skilled in the art.

The present disclosure also provides a method for alleviating a gastrointestinal barrier dysfunction-associated disorder, which includes administering to a subject in need thereof the aforesaid composition.

According to the present disclosure, the gastrointestinal barrier dysfunction-associated disorder may be selected from the group consisting of diarrhea (such as traveler's diarrhea (TD) and osmotic diarrhea), gastroenteritis (such as enteritis and viral gastroenteritis), inflammatory bowel disease (IBD) (such as ulcerative colitis (UC) and Crohn's disease), irritable bowel syndrome (IBS), typhoid fever, short bowel syndrome (SBS), small intestine bacterial overgrowth (SIBO), and combinations thereof.

In certain embodiments, the composition for alleviating a gastrointestinal barrier dysfunction-associated disorder is a pharmaceutical composition. The pharmaceutical composition may be formulated into a suitable dosage form for oral, parenteral or topical administration. The oral dosage form, parenteral dosage form, topical dosage form, and pharmaceutically acceptable carrier of this pharmaceutical composition are similar to those described above for the pharmaceutical composition for improving gastrointestinal barrier function.

In other embodiments, the composition for alleviating a gastrointestinal barrier dysfunction-associated disorder is a food product as described above.

The present disclosure further provides a method for inhibiting growth of enteric pathogenic bacteria, which includes administering to a subject in need thereof the aforesaid composition.

According to the present disclosure, the enteric pathogenic bacteria may be selected from the group consisting of *Salmonella enterica* subsp. *enterica, Listeria mronocytogenes, Escherichia coli, Vibrio parahaemolyticus, Staphylococcus aureus, Shigella boydi, Shigella dysenteriae, Klebsiella pneurmoniae, Yersinia enterocolitica, Proteus vulgaris*, and combinations thereof. In certain embodiments, the enteric pathogenic bacteria are *Salmonella enterica* subsp. *enterica, Listeria monocytogenes, Escherichia coli*, and/or *Vibrio parahaemolyticus*.

As used herein, the term "inhibition" or "inhibiting" means preventing or reducing the growth of enteric pathogenic bacteria in a subject's gastrointestinal tract.

In certain embodiments, the composition for inhibiting growth of enteric pathogenic bacteria is a pharmaceutical composition. The pharmaceutical composition may be formulated into a suitable dosage form for oral, parenteral or topical administration. The oral dosage form, parenteral dosage form, topical dosage form, and pharmaceutically acceptable carrier of this pharmaceutical composition are similar to those described above for the pharmaceutical composition for improving gastrointestinal barrier function.

In other embodiments, the composition for inhibiting growth of enteric pathogenic bacteria is a food product as described above.

The dose and frequency of administration of the composition according to the present disclosure may vary depending on the following factors: the severity of the illness or disorder to be treated, routes of administration, and age, physical condition and response of the subject to be treated. In general, the composition may be administered in a single dose or in several doses.

The present disclosure will be further described by way of the following examples. However, it should be understood that the following examples are intended solely for the purpose of illustration and should not be construed as limiting the present disclosure in practice.

Examples

General Experimental Materials:
1. Lactic acid bacterial (LAB) strains
 (a) *Lactobacillus rhamnosus* MP108
   *Lactobacillus rhamnosus* MP108, which is disclosed in CN 102604854 B and is known and readily available to the public, has been deposited at the China General Microbiological Culture Collection Center (CGMCC) of Chinese Academy of Sciences, the Institute of Microbiology (No. 1, West Beichen Rd., Chaoyang District, Beijing 100101, China) under an accession number CGMCC 21225 since Nov. 23, 2020 in accordance with the Budapest Treaty.
 (b) *Bifidobacterium longum* subsp. *infantis* BLI-02
   *Bifidobacterium longum* subsp. *infantis* BLI-02, which is disclosed in TW 1701034 B and is known and readily available to the public, has been deposited at the Bioresource Collection and Research Center (BCRC) of the Food Industry Research and Development Institute (FIRDI) (No. 331, Shih-Pin Rd., Hsinchu City 300, Taiwan) under an accession number BCRC 910812 since Jan. 18, 2018, and has also been deposited at the CGMCC of Chinese Academy of Sciences, the Institute of Microbiology, under an accession number CGMCC 15212 since Jan. 15, 2018 in accordance with the Budapest Treaty.
 (c) *Bifidobacterium animalis* subsp. *lactis* BB-115
   *Bifidobacterium animalis* subsp. *lactis* BB-115, which is disclosed in Zuo, J. D. et al. (2017), *China Modern Medicine*, Vol. 24, No. 5, has been deposited at the BCRC of the FIRDI under an accession number BCRC 911045 since Mar. 25, 2021, and has also been deposited at the CGMCC of Chinese Academy of Sciences, the Institute of Microbiology, under an accession number CGMCC 21840 since Feb. 26, 2021 in accordance with the Budapest Treaty.
 (d) Comparative LAB strains
   *Bifidobacterium animalis* subsp. *lactis* BB-12 and *Lactobacillus rhamnosus* GG (LGG) used in the following experiments were purchased from Chr. Hansen A/S, Denmark.
2. Enteric pathogenic bacterial strains
   Four enteric pathogenic bacterial strains used in the following experiments were purchased from the BCRC of the FIRDI. The relevant information regarding each of the enteric pathogenic bacterial strains is listed in Table 1 below.

TABLE 1

| Enteric pathogenic bacterial strains | Accession number |
|---|---|
| *Salmonella enterica* subsp. *enterica* | BCRC 10747 |
| *Listeria monocytogenes* | BCRC 14845 |
| *Escherichia coli* | BCRC 11634 |
| *Vibrio parahaemolyticus* | BCRC 12974 |

3. Preparation of bacterial suspension of enteric pathogenic bacterial strain
   A respective one of the four enteric pathogenic bacterial strains described in section 2 of "General Experimental Materials" was cultivated using the corresponding medium and cultivation conditions shown in Table 2 in an incubator for 20 hours to obtain a respective inoculum. Thereafter, the respective inoculum was subcultured in an amount of 2% (v/v) using the corresponding medium and cultivation conditions shown in Table 2 in an incubator, so as to obtain a bacterial suspension having a bacterial concentration ranging from $1\times10^5$ CFU/mL to $1\times10^{11}$ CFU/mL.

TABLE 2

| Enteric pathogenic bacterial strains | Medium | Cultivation conditions |
| --- | --- | --- |
| Salmonella enterica subsp. enterica | Nutrient broth (NB) (BD Bioscience, Cat. No. 234000) | 37° C., 5% $CO_2$ |
| Escherichia coli | Nutrient broth (as mentioned above) | 37° C., 5% $CO_2$ |
| Listeria monocytogenes | Brain heart infusion (BHI) medium (BD Bioscience, Cat. No. R452472) | 37° C., 5% $CO_2$ |
| Vibrio parahaemolyticus | Tryptic soy broth (TSB) (BD Bioscience, Cat. No. R112996) supplemented with 2.5% NaCl (Sigma, Cat. No. S5886) | 25° C., 5% $CO_2$ |

4. Source and cultivation of human colon adenocarcinoma cell line Caco-2

Human colon adenocarcinoma cell line Caco-2 (ATCC HTB-37™) was purchased from American Type Culture Collection (ATCC, Manassas, Va., USA). The Caco-2 cells were grown in a 10-cm Petri dish containing Dulbecco's Modified Eagle's Medium (DMEM) (Cytiva) supplemented with 10% fetal bovine serum (FBS) and 1% penicillin-streptomycin. The Caco-2 cells were cultivated in an incubator with culture conditions set at 37° C. and 5% $CO_2$. Medium change was performed every two to three days. Cell passage was performed when the cultured cells reached 80%-90% of confluence.

5. Preparation of bacterial suspension of LAB strain

A respective one of the five LAB strains described in section 1 of "General Experimental Materials" was inoculated in a MRS (De Man, Rogosa and Sharpe) broth (Cat. No. 288130, BD Difco) supplemented with 0.05% (w/w) cysteine, followed by cultivation in an incubator (37° C., 5% $CO_2$) for 24 hours to obtain a inoculum. Thereafter, the inoculum was inoculated in an amount of 2% (v/v) into a MRS broth, followed by cultivation in an incubator (37° C., 5% $CO_2$) for 24 hours.

After centrifugation at 3,000 rpm for 10 minutes, the resultant cell pellet was collected, and was then suspended in an appropriate amount of a MRS broth, thereby obtaining a bacterial suspension having a bacterial concentration of $1\times10^9$ CFU/mL, which was determined using a plate counting medium. The bacterial suspensions of the aforesaid LAB strains were used in the following experiments.

Example 1. Evaluation for the Effect of Bacterial Suspension of LAB Strain According to this Disclosure on Improving Gastrointestinal Barrier Function A. Quantitative Determination of Claudin-1 (CLDN1) Gene Expression:

The Caco-2 cells prepared in section 4 of "General Experimental Materials" were divided into 17 groups, including one control group, eight comparative groups (i.e., comparative groups S1 to S5 and D1 to D3), and eight experimental groups (i.e., experimental groups T1 to T8). Each group of the Caco-2 cells was incubated in a respective well of 6-well culture plates containing 3 mL of DMEM supplemented with 10% FBS and 1% penicillin-streptomycin at 3×10 cells/well, followed by cultivation in an incubator (37° C., 5% $CO_2$) for 11 days. Medium change was performed every 3 days.

Afterwards, the culture medium in each well was removed. The cells of each of the comparative groups S1 to S5 were added with 3 mL of the respective one of the bacterial suspensions prepared in section 5 of "General Experimental Materials", as shown in Table 3 below.

TABLE 3

| Group | LAB strain applied |
| --- | --- |
| Comparative group S1 | Lactobacillus rhamnosus MP108 |
| Comparative group S2 | Bifidobacterium longum subsp. infantis BLI-02 |
| Comparative group S3 | Bifidobacterium animalis subsp. lactis BB-115 |
| Comparative group S4 | Lactobacillus rhamnosus GG (LGG) |
| Comparative group S5 | Bifidobacterium animalis subsp. lactis BB-12 |

In addition, the bacterial suspensions of Lactobacillus rhamnosus MP108, Bifidobacterium longum subsp. infantis BLI-02, and Bifidobacterium animalis subsp. lactis BB-115 prepared in section 5 of "General Experimental Materials" (in suitable amounts) were mixed in different number ratios shown in Table 4, so as to obtain 11 suspension mixtures (i.e., suspension mixtures D1 to D3 and T1 to T8). Each of the eleven suspension mixtures had a total bacterial concentration of $1\times10^9$ CFU/mL.

The cells of each of the comparative groups D1 to D3 and the experimental groups T1 to T8 were added with 3 mL of the respective one of the suspension mixtures, as shown in Table 4 below. The cells of the control group were added with DMEM without any bacterial suspension.

TABLE 4

| Group | Suspension mixture | Number ratio of Lactobacillus rhamnosus MP108, Bifidobacterium longum subsp. infantis BLI-02, and Bifidobacterium animalis subsp. lactis BB-115 |
| --- | --- | --- |
| Comparative group D1 | D1 | 0:1:1 |
| Comparative group D2 | D2 | 1:0:1 |
| Comparative group D3 | D3 | 1:1:0 |
| Experimental group T1 | T1 | 1:0.11:1 |
| Experimental group T2 | T2 | 1:0.2:1 |
| Experimental group T3 | T3 | 1:0.67:1 |
| Experimental group T4 | T4 | 1:1:0.67 |
| Experimental group T5 | T5 | 1:1:1 |
| Experimental group T6 | T6 | 1:1.5:1.5 |
| Experimental group T7 | T7 | 1:5:5 |

TABLE 4-continued

| Group | Suspension mixture | Number ratio of Lactobacillus rhamnosus MP108, Bifidobacterium longum subsp. infantis BLI-02, and Bifidobacterium animalis subsp. lactis BB-115 |
|---|---|---|
| Experimental group T8 | T8 | 1:9:9 |

Each group was cultivated at 37° C. and 5% $CO_2$ for 6 hours. Next, the cell culture of each group was subjected to total RNA extraction using Total RNA Extraction Miniprep System (VIOGENE, Cat. No. GR1001) in accordance with the manufacturer's instructions. The resultant RNA of the respective group was used as a template for synthesizing cDNA by reverse transcription polymerase chain reaction (RT-PCR) using GoScript™ Reverse Transcriptase (Promega, Cat. No. A5003).

The thus obtained cDNA, serving as a DNA template, was subjected to quantitative real-time PCR based on SYBR-Green I fluorescence, which was performed on a StepOne-Plus™ real-time PCR system (Applied Biosystems) using a designed primer pair specific for CLDN1 gene (as described in Y. Jin and A. T. Blikslager, (2016), *Am. J. Physiol. Cell Physiol.*, 311 (6):C996-C1004) shown in Table 5 and the reaction conditions shown in Table 6. Glyceraldehyde-3-phosphate dehydrogenase (GAPDH) gene was used as an endogenous control in the quantitative analysis of real-time PCR to normalize the gene expression data.

TABLE 5

| Target gene | Primer | Nucleotide sequence (5'-3') | Size of PCR product (bp) |
|---|---|---|---|
| CLDN1 gene (GenBank accession no. AF115546.1) | Forward primer CLDN1-F | gcgcgatatttcttcttgcagg (SEQ ID NO: 1) | 112 |
| | Reverse primer CLDN1-R | ttcgtacctggcattgactgg (SEQ ID NO: 2) | |
| GAPDH gene (NCBI accession no. NM_002046.2) | Forward primer GAPDH-F | gaaggtgaaggtcggagt (SEQ ID NO: 3) | 225 |
| | Reverse primer GAPDH-R | gaagatggtgatggatttc (SEQ ID NO: 4) | |

TABLE 6

| Reaction mix | Volume (μL) |
|---|---|
| cDNA (0.1 μg/μL) | 2 |
| Forward primer (10 μM) | 0.8 |
| Reverse primer (10 μM) | 0.8 |
| qPCRBIO SyGreen Mix (PCR Biosystems, Cat. No. PB20.12-05) | 10 |
| Deionized water | 6.4 |

Operation conditions: forty cycles of the following reactions: denaturation at 95° C. for 3 minutes, annealing at 95° C. for 5 seconds, and extension at 60° C. for 30 seconds.

The resultant PCR product was subjected to determination of fluorescence intensity, followed by calculating the cycle threshold (Ct) value of CLDN1 gene. Quantitative real-time PCR data were analyzed using the comparative Ct method. Briefly, the Ct value of CLDN1 gene in each group was normalized with that of GAPDH gene, and the relative mRNA expression level of CLDN1 gene was further calculated using the following Equation (I):

$$A = B - C \qquad (I)$$

where A=relative mRNA expression level of CLDN1 gene

B=normalized ct value of CLDN1 gene in respective group

C=normalized ct value of CLDN1 gene in control group

All the experiments described above were performed in triplicate. The experimental data are expressed as mean±standard deviation (SD) and were analyzed using one-way analysis of variance (ANOVA) so as to assess the difference between all the groups. Statistical significance is indicated by $p<0.05$.

Referring to FIG. 1, the relative mRNA expression levels of CLDN1 gene determined in the experimental groups T2 to T8 were higher than those determined in the comparative groups S1 to S5. Moreover, the relative mRNA expression levels of CLDN1 gene determined in the experimental groups T2 to T7 were higher than those determined in the comparative groups D1 to D3.

The aforesaid result suggests that *Lactobacillus rhamnosus* P1108, *Bifidobacterium longum* subsp. *infantis* BLI-02, and *Bifidobacterium animals* subsp. *lactis* BB-115, when mixed in a specific number ratio ranging from 1:0.2:0.67 to 1:9:9 to prepare a suspension mixture, can synergistically exhibit satisfactory efficacy in enhancing CLDN1 gene expression, and hence are capable of improving gastrointestinal barrier function by increasing the intestinal epithelial tight junction protein CLDN1 level.

B. Transepithelial Electrical Resistance (TEER) Assay

The Caco-2 cells prepared in section 4 of "General Experimental Materials" were divided into 7 groups, including five comparative groups (i.e., comparative groups S1 to S5) and two experimental groups (i.e., experimental groups T1 to T2). Each group of the Caco-2 cells was seeded at a concentration of $3\times10^5$ cells per well into a respective permeable Transwell, insert (Corning Inc.) for 6-well plates. Each of the Transwell® inserts had a polycarbonate membrane (pore size: 0.4 μm) and contained 2.5 mL of DMEM. Next, the Transwell-inserts were placed into the 6-well plates that contained 1.5 mL of DMEM in each well, followed by cultivation in an incubator (37° C., 5% $CO_2$) for 6 days, and medium change was performed every 3 days, so that the Caco-2 cells formed a cell monolayer in the Transwell® inserts. Afterwards, the culture medium in each Transwell® insert was removed, and the respective Transwell® insert was washed with phosphate-buffered saline (PBS) two times, followed by adding a fresh DMEM medium. Next, each group was subjected to determination of TEER level using an EVOM2 voltohmmeter (WPI, Sarasota, FL, USA) equipped with a STX2 electrode.

Thereafter, the culture medium in each Transwell® insert was removed. The Caco-2 cell monolayer of each of the comparative groups 31 to S5 was added with 3 mL of the respective one of the bacterial suspensions prepared in section 5 of "General Experimental Materials", as shown in Table 7 below. The Caco-2 cell monolayers of the experimental groups T1 and T2 were respectively added with 3 mL of the suspension mixtures T3 and T5 prepared in section A of this example, as shown in Table 8 below.

TABLE 7

| Group | LAB strain applied |
| --- | --- |
| Comparative group S1 | Lactobacillus rhamnosus MP108 |
| Comparative group S2 | Bifidobacterium longum subsp. infantis BLI-02 |
| Comparative group S3 | Bifidobacterium animalis subsp. lactis BB-115 |
| Comparative group S4 | Lactobacillus rhamnosus GG (LGG) |
| Comparative group S5 | Bifidobacterium animalis subsp. lactis BB-12 |

TABLE 8

| Group | Suspension mixture | Number ratio of Lactobacillus rhamnosus MP108, Bifidobacterium longum subsp. infantis BLI-02, and Bifidobacterium animalis subsp. lactis BB-115 |
| --- | --- | --- |
| Experimental group T1 | T3 | 1:0.67:1 |
| Experimental group T2 | T5 | 1:1:1 |

Each group was cultivated in an incubator (37° C., 5,D $CO_2$) for 5 hours. After removal of the culture medium in each Transwell® insert, each group was subjected to determination of TEER level according to the procedure described above.

The TEER increase rate (%) of each group was calculated by substituting the TEER level, which was determined before and after treatment with the bacterial suspension or the suspension mixture, into the following Equation (II):

$$D=[(E-F)/F]\times 100 \quad (II)$$

where D=TEER increase rate (%)
  E=TEER level determined after treatment with the bacterial suspension or the suspension mixture
  F=TEER level determined before treatment with the bacterial suspension or the suspension mixture All the experiments described above were performed in triplicate. The experimental data are expressed as mean±SD and were analyzed using one-way ANOVA so as to assess the difference between all the groups. Statistical significance is indicated by $p<0.05$.

Figure 2:
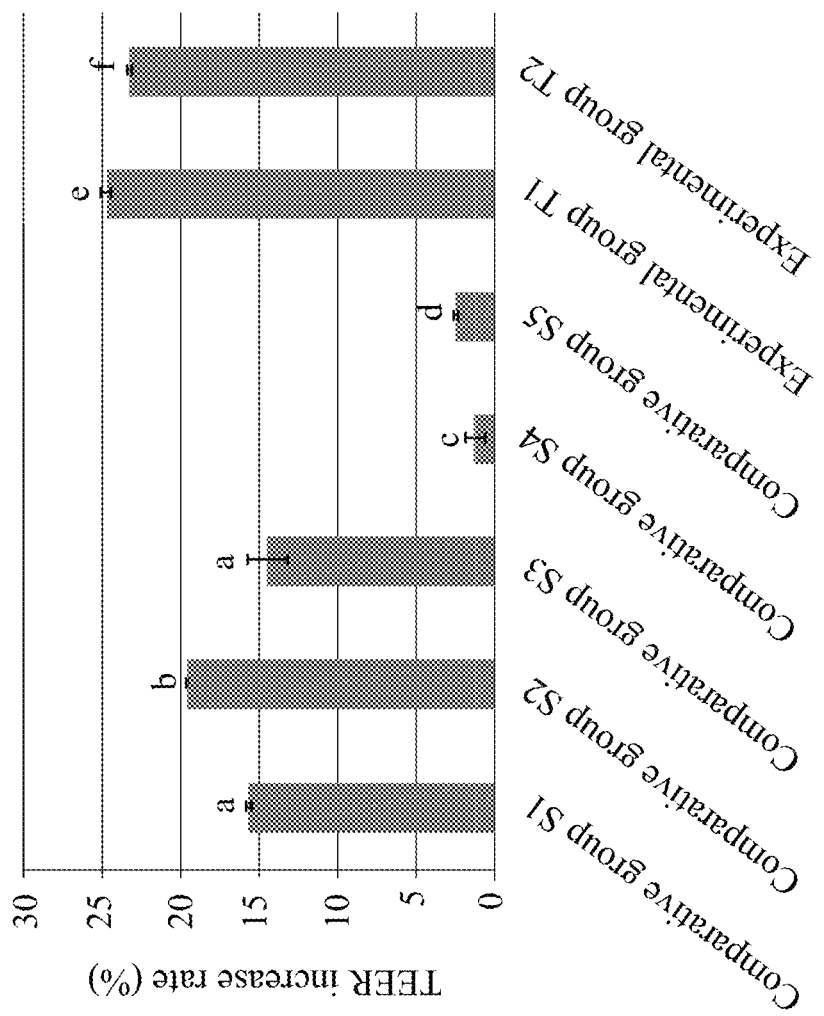
FIG. 2 shows a transepithelial electrical resistance (TEER) increase rate in each group of Example 1, infra, in which: the English letters indicate the results of statistical analysis; if two groups have any same English letter, there is no significant difference between the two groups; and if two groups do not have any same English letter, there is a significant difference between the two groups ($p<0.05$)

Referring to FIG. 2, the TEER increase rates determined in the experimental groups T1 to T2 were higher than those determined in the comparative groups S1 to S5. The aforesaid result suggests that Lactobacillus rhamnosus MP108, Bifidobacterium longum subsp. infantis BLI-02, and Bifidobacterium animalis subsp. lactis BB-115, when mixed in a specific number ratio ranging from 1:0.67:1 to 1:1:1 to prepare a suspension mixture, can synergistically exhibit satisfactory efficacy in increasing the TEER level, and hence are capable of improving gastrointestinal barrier function.

Example 2. Intestinal Adhesion Assay

Experimental Procedures:
Intestinal adhesion assay was conducted using a method slightly modified from that described by Hsieh, P. S. et al. (2021), Exp. Ther. Med., 21(3):168. Briefly, a sterilized cover slip was placed into a respective well of a 6-well culture plate that contained 5 mL of DMEM in each well. The Caco-2 cells prepared in section 4 of "General Experimental Materials" were divided into 4 groups, including two comparative groups (i.e., comparative groups S1 to S2) and two experimental groups (i.e., experimental groups T1 to T2). Each group of the Caco-2 cells was incubated in a respective well of the 6-well culture plate at 3×10 cells/well, followed by cultivation in an incubator (37° C., 5% $CO_2$) until the cultured cells reached 100% of confluence, so that the Caco-2 cells formed a cell monolayer in the respective well. Next, medium change was performed by adding a fresh DMEM medium into the 6-well culture plate, followed by cultivation in an incubator (37° C., 5% C02) for 1 hour. Afterwards, the culture medium in each well was removed, and the Caco-2 cell monolayer of each group was washed with PBS two times.

The thus formed Caco-2 cell monolayers of the experimental groups T1 and T2 were respectively added with 3 mL of the suspension mixtures T3 and T5 prepared in section A of Example 1. In addition, the thus formed Caco-2 cell monolayers of the comparative groups S1 and S2 were respectively added with 3 mL of the bacterial suspensions of Lactobacillus rhamnosus GG (LGG) and Bifidobacterium animalis subsp. lactis BB-12 prepared in section 5 of "General Experimental Materials". Each group was further added with 1.5 mL of a fresh DMEM medium, followed by cultivation in an incubator (37° C., 5% $CO_2$) for 2 hours.

Thereafter, the culture medium in each group was removed, followed by washing with an appropriate amount of PBS. A suitable amount of methanol (absolute) was added to fix the Caco-2 cell monolayer for 10 minutes, followed by conducting Gram staining using a staining protocol well-known to those skilled in the art. The number of the stained bacterial cells attached to the Caco-2 cell monolayer was counted under an optical microscope (Carl Zeiss MicroImaging, Inc.) at 1,500× magnification.

All the experiments described above were performed in triplicate. The experimental data are expressed as mean±SD and were analyzed using Student's t-test so as to assess the difference between all the groups. Statistical significance is indicated by $p<0.05$.

Figure 3:
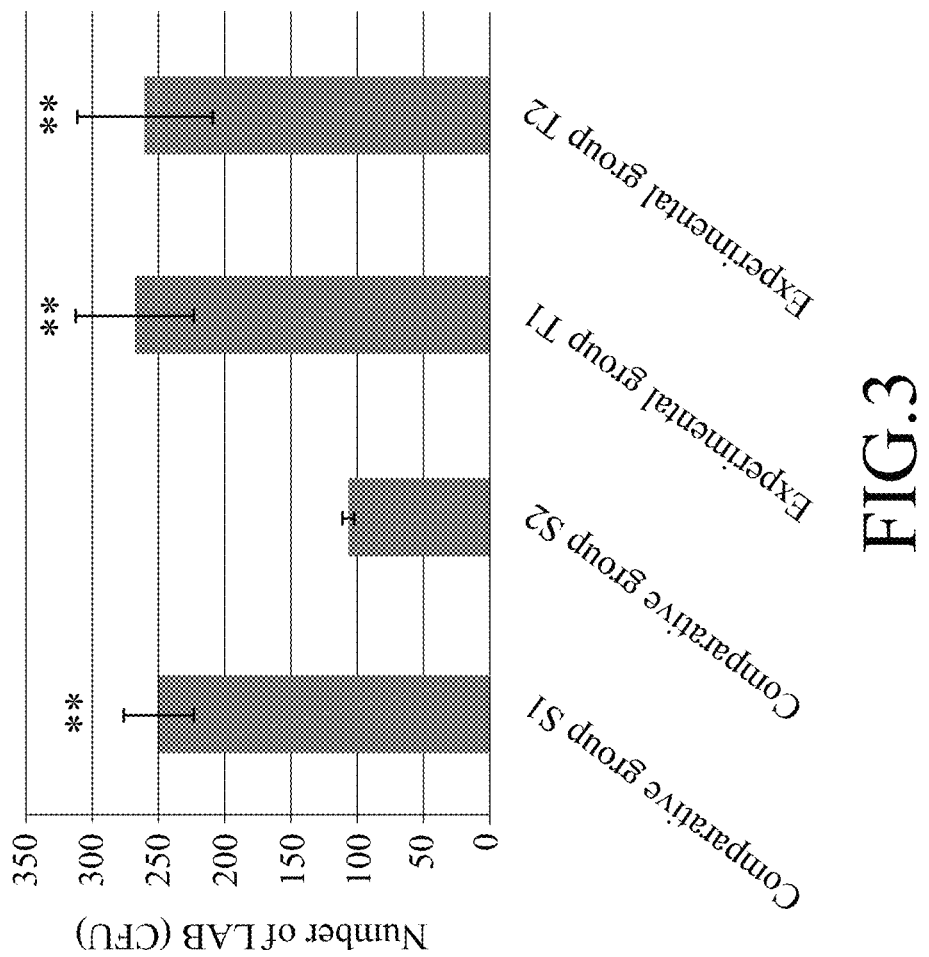
FIG. 3 shows the number of lactic acid bacteria (LAB) in each group of Example 2, infra, in which the symbol "**" represents $p<0.01$ (compared with the comparative group S2).

Results:
Referring to FIG. 3, the numbers of LAB determined in the experimental groups T1 and T2 were significantly higher than that determined in the comparative group S2, indicating that Lactobacillus rhamnosus MP108, Bifidobacterium longum subsp. infantis BLI-02, and Bifidobacterium animalis subsp. lactis BB-115, when mixed in a specific number ratio ranging from 1:0.67:1 to 1:1:1 to prepare a suspension mixture, can synergistically exhibit satisfactory intestinal adhesion ability, and hence are capable of providing an excellent and sustained protective effect in the gastrointestinal tract.

Example 3. Evaluation for the Effect of Bacterial Suspension of LAB Strain According to this Disclosure Against Enteric Pathogenic Bacterial Strain Materials and Methods:
A. Preparation of MRS Agar Plate
The MRS agar plate used in the following experiments was prepared by adding 1.5% (w/v) of agar powder to a MRS broth and using technology well-known to those skilled in the art.
B. Preparation of Top Agar Medium
A respective one of the three mediums described in Table 2 was added with 1.5% (w/v) of agar powder, followed by sterilization at 121° C. for 15 minutes. The respective resultant melted agar medium (serving as a top agar medium) was then placed in a 45° C. water bath for subsequent use.

C. Determination of Anti-Pathogenic Efficacy

The anti-pathogenic efficacy of the bacterial suspension of LAB was determined using a double agar overlay method slightly modified from that described by Chen, Y. T. et al. (2020), *Lett. Appl. Microbiol.*, 70(4):310-317. Briefly, the bacterial suspension of *Lactobacillus rhamnosus* GG (LGG) prepared in section 5 of "General Experimental Materials" (in a suitable amount) served as a comparative group, and the suspension mixtures T3 and T5 prepared in section A of Example 1 (in a suitable amount) respectively served as experimental groups 1 and 2.

Thereafter, about 1 mL of the bacterial suspension of the comparative group or about 1 mL of the suspension mixture of the respective experimental group was collected using a sterilized cotton swab by dipping, and then a line with a width of approximately 2 cm was formed along the diameter of the MRS agar plate prepared in section A of this example using the cotton swab with the collected suspension or suspension mixture, followed by cultivation in an incubator (37° C.) for 48 hours, so that the respective group formed a growth zone with a width of approximately 2 cm on the surface of the MRS agar medium. In addition, a MRS broth being free from any LAB strain (serving as a blank control group) was subjected to the same procedure.

Next, the melted NB agar medium (i.e., the top agar medium) prepared in section B of this example was poured into the MRS agar plate of each group to evenly overlay the MRS agar medium. After the NB agar medium had solidified to form a double-layer agar (DLA) medium, the bacterial suspension of *Salmonella enterica* subsp. *enterica* prepared in section 3 of "General Experimental Materials" was collected using a sterilized cotton swab by dipping, and was then evenly coated onto the surface of the DLA medium (i.e., the top agar medium) of the respective group, followed by cultivation in an incubator (37° C., 5% CO$_2$) for 24 hours. The effect of each group in inhibiting the growth of *Salmonella enterica* subsp. *enterica* was evaluated by measuring the width of the inhibition zone formed by each group on the surface of the DLA medium.

The inhibitory effects of each group on *Escherichia coli*, *Listeria monocytogenes*, and *Vibrio parahaemolyticus* were determined according to the procedure described above, except that the bacterial suspension of *Escherichia coli* was coated onto the surface of the DLA medium containing the NB agar medium as a top agar medium, the bacterial suspension of *Listeria monocytogenes* was coated onto the surface of the DLA medium containing the BHI agar medium as a top agar medium, or the bacterial suspension of *Vibrio parahaemolyticus* was coated onto the surface of the DLA medium containing the TSB agar medium supplemented with 2.5% NaCl as a top agar medium.

The anti-pathogenic efficacy was assessed by scoring on a scale from 0 to 6. The higher scale indicated the higher anti-pathogenic efficacy, i.e. scale 0 indicated that the width of the inhibition zone was 0 cm, scale 1 indicated that the width of the inhibition zone was >0 cm to <2 cm, scale 2 indicated that the width of the inhibition zone was 2 cm to <3 cm, scale 3 indicated that the width of the inhibition zone was 3 cm to <4 cm, scale 4 indicated that the width of the inhibition zone was 4 cm to <5 cm, scale 5 indicated that the width of the inhibition zone was 5 cm to <8.5 cm, and scale 6 indicated that the width of the inhibition zone was >8.5 cm.

Results:

Table 9 shows the anti-pathogenic efficacy determined in each group. As shown in Table 9, for each enteric pathogenic bacterial strain, the anti-pathogenic efficacy determined in each of the experimental groups 1 to 2 was significantly higher than that determined in the comparative group.

The aforesaid result suggests that *Lactobacillus rhamnosus* MP108, *Bifidobacterium longum* subsp. *infantis* BLI-02, and *Bifidobacterium animalis* subsp. *lactis* BB-115, when mixed in a specific number ratio ranging from 1:0.67:1 to 1:1:1 to prepare a suspension mixture, can synergistically exhibit satisfactory efficacy in inhibiting growth of enteric pathogenic bacteria.

TABLE 9

| | Anti-pathogenic efficacy | | | |
|---|---|---|---|---|
| Group | *Salmonella enterica* subsp. *enterica* | *Listeria monocytogenes* | *Escherichia coli* | *Vibrio parahaemolyticus* |
| Blank control group | 0 | 0 | 0 | 0 |
| Comparative group | 3 | 3 | 4 | 4 |
| Experimental group 1 | 5 | 4 | 5 | 5 |
| Experimental group 2 | 5 | 4 | 6 | 5 |

Summarizing the above test results, it is clear that *Lactobacillus rhamnosus* MP108, *Bifidobacterium longum* subsp. *infantis* BLI-02, and *Bifidobacterium animalis* subsp. *lactis* BB-115, when mixed in a specific number ratio ranging from 1:0.2:0.67 to 1:9:9 to prepare a suspension mixture, are capable of effectively improving gastrointestinal barrier function and inhibiting growth of enteric pathogenic bacteria, and can synergistically exhibit satisfactory intestinal adhesion ability, and hence can alleviate a gastrointestinal barrier dysfunction-associated disorder.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for improving gastrointestinal barrier function, comprising administering to a subject in need thereof a composition containing *Lactobacillus rhamnosus* MP108, *Bifidobacterium longum* subsp. *infantis* BLI-02, and *Bifidobacterium animalis* subsp. *lactis* BB-115, which are deposited at the China General Microbiological Culture Collection Center (CGMCC) respectively under accession numbers CGMCC 21225, CGMCC 15212, and CGMCC 21840,
  wherein a number ratio of *Lactobacillus rhamnosus* MP108, *Bifidobacterium longum* subsp. *infantis* BLI-02, and *Bifidobacterium animalis* subsp. *lactis* BB-115 is 1:0.67:1.

2. The method as claimed in claim 1, wherein the improvement of the gastrointestinal barrier function includes at least one of the following: improving a structure and function of gastrointestinal tract epithelium, protection against gastrointestinal pathogenic bacteria infection, and regulating gastrointestinal microflora.

3. The method as claimed in claim 1, wherein the composition is formulated as a food product.

4. The method as claimed in claim 1, wherein the composition is formulated as a pharmaceutical composition.

5. The method as claimed in claim 4, wherein the pharmaceutical composition is in a dosage form selected from the group consisting of an oral dosage form, a parenteral dosage form, and a topical dosage form.

6. A method for alleviating a gastrointestinal barrier dysfunction-associated disorder, comprising administering to a subject in need thereof a composition containing *Lactobacillus rhamnosus* MP108, *Bifidobacterium longum* subsp. *infantis* BLI-02, and *Bifidobacterium animalis* subsp. *lactis* BB-115, which are deposited at the China General Microbiological Culture Collection Center (CGMCC) respectively under accession numbers CGMCC 21225, CGMCC 15212, and CGMCC 21840,
  wherein a number ratio of *Lactobacillus rhamnosus* MP108, *Bifidobacterium longum* subsp. *infantis* BLI-02, and *Bifidobacterium animalis* subsp. *lactis* BB-115 is 1:0.67:1.

7. The method as claimed in claim 6, wherein the gastrointestinal barrier dysfunction-associated disorder is selected from the group consisting of diarrhea, gastroenteritis, inflammatory bowel disease (IBD), irritable bowel syndrome (IBS), typhoid fever, short bowel syndrome (SBS), small intestine bacterial overgrowth (SIBO), and combinations thereof.

8. The method as claimed in claim 6, wherein the composition is formulated as a food product.

9. The method as claimed in claim 6, wherein the composition is formulated as a pharmaceutical composition.

10. The method as claimed in claim 9, wherein the pharmaceutical composition is in a dosage form selected from the group consisting of an oral dosage form, a parenteral dosage form, and a topical dosage form.

* * * * *